US00PP11025P

United States Patent [19]

Meilland

[11] Patent Number: Plant 11,025

[45] Date of Patent: Aug. 3, 1999

[54] MINIATURE ROSE PLANT NAMED 'MEIPTIMA'

[75] Inventor: Alain A. Meilland, Antibes, France

[73] Assignee: CP (Delaware), Inc., Wilmington, Del.

[21] Appl. No.: 09/021,507

[22] Filed: Feb. 10, 1998

[30] Foreign Application Priority Data

Jul. 23, 1997 [FR] France ..... 15594

[51] Int. Cl.[6] ..... A01H 5/00

[52] U.S. Cl. ..... Plt./123

[58] Field of Search ..... Plt./116, 123, 121, Plt./128

[56] References Cited

U.S. PATENT DOCUMENTS

P.P. 6,141 3/1988 Bennett ..... Plt./123

P.P. 7,187 3/1990 Bennett ..... Plt./116

*Primary Examiner*—Howard J. Locker

*Attorney, Agent, or Firm*—Burns, Doane, Swecker & Mathis, L.L.P.

[57] ABSTRACT

A new and distinct variety of rose plant of the Miniature Class is provided which abundantly forms attractive double lavender blossoms on a substantially continuous basis. The blossoms tend to be borne above the foliage where they are clearly visible. A dense, narrow and bushy growth habit is exhibited that renders the plant well suited for growing as attractive ornamentation in the landscape. The buds are conical in configuration and are elegantly shaped. The foliage is dark green and contrasts nicely with the lavender blossoms.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was the product of the pollination of the 'Keimove' variety (non-patented in the United States) and the 'Ruiblun' variety (non-patented in the United States). The male parent (i.e., the pollen parent) of the new variety was the 'Lavender Jewel' variety (U.S. Plant Pat. No. 4,480). The parentage of the new variety can be summarized as follows:

('Keimove'×'Ruiblun')×'Lavender Jewel'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms conical elegantly-shaped lavender buds,
(b) forms in abundance on a substantially continuous basis attractive double lavender blossoms that tend to be borne above the foliage,
(c) exhibits a dense, narrow and bushy growth habit, and
(d) forms attractive semi-glossy dark green foliage.

The blossoms are commonly positioned above the foliage where they are unobstructed to view, and contrast nicely with the dark green foliage.

The new variety well meets the needs of the horticultural industry. It is particularly well-suited for use as attractive ornamentation in the landscape.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meiptima' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were nine months of age and were observed during March while growing on their own roots outdoors at LeCannet des Maures, Var, France.

DETAILED DESCRIPTION

Figures 1, 2, 3, 4, 5, 6, 7, 8, 9, 10, 11, 12, 13, 14, 15:
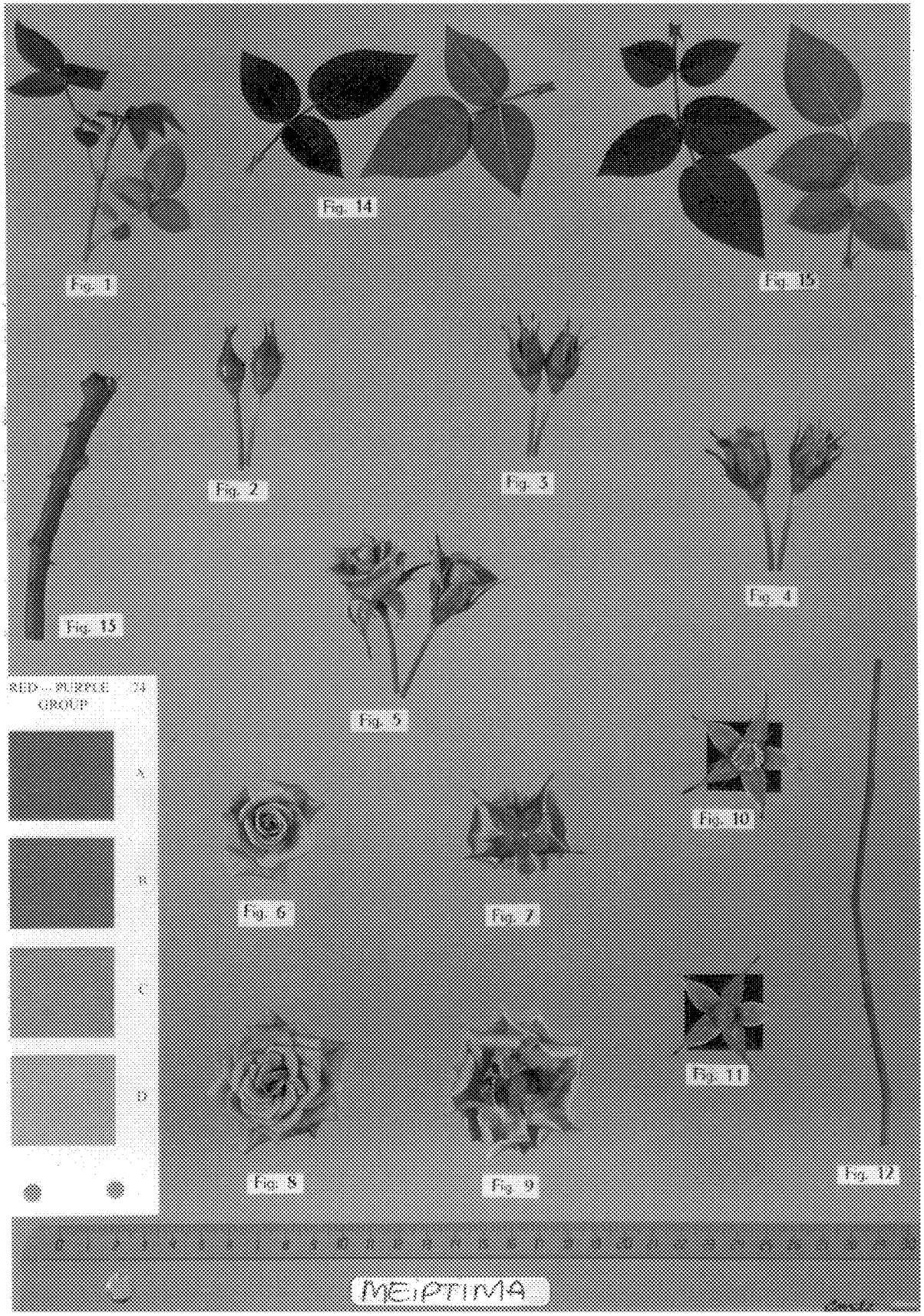
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates specimens of two flowers during the course of opening.
FIG. 6 illustrates a specimen of an open flower — plan — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of two leaves with three leaflets with the upper surface being shown at the left and the under surface being shown at the right.
FIG. 15 illustrates specimens of two leaves with five leaflets with the upper surface being shown at the left and the under surface being shown at the right.

The chart used in the identification of the colors is that of The Royal Horticultural Society (R.H.S. Colour Chart). The terminology which precedes reference to the chart has been added to indicate the corresponding colors in more common terms. The description is based on nine-month-old specimens of the new variety which were observed during March while growing on their own roots outdoors at LeCannet des Maures, Var, France.

Class: Miniature.

Plant:

*Height.*—Approximately 45 to 50 cm. on average at the end of the growing season.

*Habit.*—Narrow and bushy.

Branches:

*Color.*—Young stems: near Yellow-Green Group 146B. Adult wood: near Yellow-Green Group 147A.

*Thorns.*—Size: small. Quantity: relatively few (as illustrated). Color: greenish on young stems and pinkish-green on adult wood.

Leaves:

*Petioles.*—Upper surface: slightly glandular. Under surface: bears some small thorns.

*Stipules.*—Adnate, pectinate, narrow and linear.

*Leaflets.*—Number: 3, 5 (most often), and 7. Shape: oval. Texture: very consistent. Serration: regular. General appearance: dense, medium green, and semi-glossy. Color (young foliage): Upper surface: near Yellow-Green Group 147A. Under surface: near Yellow-Green Group 148B. Color (adult foliage): Upper surface: near Yellow-Green Group 147A. Under surface: near Yellow-Green Group 147B.

Inflorescence:

*Number of flowers.*—Commonly approximately 2 to 5 per stem.

*Peduncle.*—Light green in coloration, and the length is approximately 4 cm. on average.

*Sepals.*—Upper surface: greenish in coloration. Under surface: medium green in coloration.

*Buds.*—Shape: conical, well-shaped and elegant. Length: approximately 1.5 cm. on average. Size: medium for class. Bearing: commonly above the foliage. Color upon opening: Upper surface: Lavender, Red-Purple Group 74C. Under surface: Lavender, Red-Purple Group 74C.

*Flower.*—Form: cup-shaped, and double with reflexed edges. Diameter: approximately 6 to 7 cm. on average. Color (when opening begins): Upper surface: Lavender, Red-Purple Group 74C and suffused with Red-Purple Group 74D on the edges of the petals. Under surface: Lavender, Red-Purple Group 74C and suffused with Red-Purple Group 74D on the edges of the petals. Color (when blooming): Upper surface: Lavender, Red-Purple Group 74C and suffused with Red-Purple Group 74D on the edges of the petals. Under surface: Lavender, Red-Purple Group 74C and suffused with Red-Purple Group 74D on the edges of the petals. Color (at end of opening): Upper surface: Lavender, Red-Purple Group 74C and widely suffused with Red-Purple Group 74D. Under surface: Lavender, Red-Purple Group 74C and widely suffused with Red-Purple Group 74D. Fragrance: none. Petal number: approximately 37 to 39 on average. Petal drop: good. Anthers: light yellow in coloration. Stamen number: approximately 98 on average. Filaments: whitish in coloration. Pistil number: approximately 52 on average. Stigmas: pink in coloration. Styles: whitish in coloration. Receptacle: greenish in coloration, and in longitudinal section in the shape of a funnel. Lasting quality: long on the plant.

Development:

*Vegetation.*—Strong.

*Blooming.*—Abundant and substantially continuous.

*Resistance to diseases.*—Good.

I claim:

1. A new and distinct variety of Miniature rose plant characterized by the following combination of characteristics:

(a) forms conical elegantly-shaped lavender buds,
(b) forms in abundance on a substantially continuous basis attractive double lavender blossoms that tend to be borne above the foliage,
(c) exhibits a dense, narrow and bushy growth habit, and
(d) forms attractive semi-glossy dark green foliage;

substantially as herein shown and described.

* * * * *

RED—PURPLE GROUP 74
A
B
C
D

MEIPTIMA